United States Patent [19]
Stiefel

[11] Patent Number: 5,166,168
[45] Date of Patent: Nov. 24, 1992

[54] TOPICAL BIOTIN COMPOSITIONS AND METHOD OF USE

[75] Inventor: Werner K. Stiefel, Coral Gables, Fla.

[73] Assignee: Stiefel Laboratories, Inc., Coral Gables, Fla.

[21] Appl. No.: 705,663

[22] Filed: May 24, 1991

[51] Int. Cl.$^5$ .......................................... A61K 31/415
[52] U.S. Cl. .................................................... 514/387
[58] Field of Search ....................................... 514/387

[56] References Cited

PUBLICATIONS

The Merck Index, 9th ed., 1976, pp. 161-162, & 1244.
Chemical Abstracts 112:83853k (1990).
Chemical Abstracts 109:237012n (1988).
Chemical Abstracts 112:84170x (1990).
"Treatment of Brittle Fingernails and Onychoschizia With Biotin: Scanning Electron Microscopy", *J. Am. Acad. Dermatol.*, 23, 1127-1132 (1990).
*Merck Index*, 11th ed., Monograph No. 1244.
*Food Chemicals Codex*, 3rd Ed., pp. 38-39.

*Primary Examiner*—Leonard Schenkman
*Attorney, Agent, or Firm*—Mathews, Woodbridge & Collins

[57] ABSTRACT

Topical compositions of biotin or a pharmaceutically acceptable salt thereof are used in the treatment of ungual pathologies and to harden ungues in humans.

5 Claims, No Drawings

TOPICAL BIOTIN COMPOSITIONS AND METHOD OF USE

DETAILED DESCRIPTION

The present invention pertains to topical preparations for the treatment of ungual pathologies in humans and to methods for treating ungual pathologies and hardening ungues. In particular, the invention relates to topical compositions including biotin or a pharmaceutically acceptable salt thereof.

A great variety of pathologies affect the ungues (i.e. fingernails or toenails) of humans. Ungual pathologies in humans include nail alterations in primary skin diseases (e.g. psoriasis, lichen planus, alopecia areata, Darier's disease), bacterial, viral and fungal infections (e.g. acute paronychia, chronic paronychia, Pseudomonas infection, herpetic whitlow, onychomycosis), trauma (e.g. onycholysis, nail and cuticle biting, nail plate excoriation, hangnail, ingrown toenail, subungual hematoma, nail hypertrophy, white spots or bands, distal plate splitting, habit-tic deformity, median nail distrophy, pincer nails), internal diseases (e.g. Beau's lines, yellow nail syndrome, spoon nails, finger clubbing, Terry's nails), congenital anomalies, color changes, and tumors (e.g. warts, digital mucous cysts, pyogenic granuloma, nevi and melanoma).

The chemical name for biotin is hexahydro-2-oxo-1H-thieno[3,4-d]imidazole-4-pentanoic acid, and its chemical structure is:

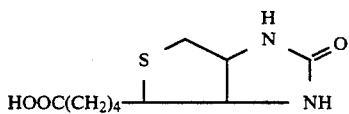

A member of the B-complex, biotin is known to be essential to human metabolism and is synthesized by human intestinal microflora. Endogenous biotin can be supplemented with orally administered biotin. For example, biotin has been incorporated into several multivitamin formulations.

Oral biotin has been used to treat seborrheic dermatitis, Leiner's disease, and hair growth disorders in humans, and various hoof conditions in animals. A study published in the *Journal of the American Academy of Dermatology* found daily oral doses of biotin helped to improve the condition of splitting and brittle nails in women. Colombo et al., "Treatment of Brittle Fingernails and Onychoschizia With Biotin: Scanning Electron Microscopy," *J. Am. Acad. Dermatol.*, 23, 1127–1132 (1990).

The present invention relates to topical compositions for the treatment of ungual pathologies in humans comprising an effective amount of biotin or a pharmaceutically acceptable salt thereof.

The invention also relates to the method of treating ungual pathologies in humans by topically applying to the affected unguis an effective amount of biotin or a pharmaceutically acceptable salt thereof.

Finally, the invention relates to the method of hardening ungues in humans by topically applying to the ungues an effective amount of biotin or a pharmaceutically acceptable salt thereof.

The composition and methods of the present invention can employ biotin or alternatively a pharmaceutically acceptable salt of biotin. Any pharmaceutically acceptable salt known in the art can be used. Typical salts include alkali metal, alkaline earth metal, ammonia, or organic amine salts as, for example, sodium, potassium, magnesium, calcium, protonated amines such as those derived from ethylamine, triethylamine, ethanolamine, diethylamino-ethanol, ethylenediamine, piperidine, morpholine, 2-piperidinoethanol, benzylamine, procaine and the like.

The treatment of ungual pathologies or the hardening of ungues in humans preferably is carried out employing compositions in which an effective amount of biotin or a pharmaceutically acceptable salt thereof is admixed with an ungually acceptable pharmaceutical carrier. Suitable pharmaceutical carriers are those which are typically employed in the topical application of pharmaceuticals and cosmetics. Examples of topically applied pharmaceutical carriers include ointments, creams, lotions, solutions, gels, films or film-forming fluids (e.g. flexible collodion, nail polish), pastes, plasters, patches, pads and bandages.

The composition and methods of this invention utilize an effective amount of biotin or a pharmaceutically acceptable salt thereof. Typically, an effective amount is from about 0.01 to about 20.00% by weight of the total composition.

The composition of the present invention can further include an effective amount of at least one penetration enhancer. Penetration enhancers are materials which enhance or increase permeability at the site of application. Any penetration enhancer known in the art can be employed. Suitable penetration enhancers include menthol, propylene glycol, dimethyl sulfoxide (DMSO), dimethyl acetamide (DMA), dimethylformamide (DMFA), and azone.

In the treatment of ungual pathologies and the hardening of ungues, compositions according to the present invention comprising biotin or a pharmaceutically acceptable salt thereof should be topically applied to the affected unguis or ungues from one to six times daily. The precise regimen in each case will be determined by the physician based upon the exact diagnosis, the severity of the pathology, its responsiveness to treatment, etc.

The following examples will serve to further typify the nature of the invention but should not be construed as a limitation on the scope thereof, which is defined solely by the appended claims.

EXAMPLE 1

An ointment is prepared by combining 10.0% (w/w) of biotin and 90.0% (w/w) of white petrolatum and blending with a suitable mixer until uniform.

EXAMPLE 2

Biotin, 0.025% (w/w), is dissolved in a uniform mixture of 5.000% (w/w) of propylene glycol and 94.975% (w/w) of purified water to form a topical solution.

EXAMPLE 3

A solution is prepared from the following components:

| Ingredient | Amount (% w/w) |
| --- | --- |
| Biotin | 0.100 |
| Menthol | 0.100 |
| Carbomer | 0.500 |
| Alcohol | 10.000 |
| Sodium Hydroxide | q.s. to pH about 5 |

-continued

| Ingredient | Amount (% w/w) |
| --- | --- |
| Purified Water | q.s. to 100.000 |

In a first container, purified water is warmed and the carbomer is added to the water and dispersed with mixing. In a second container, the menthol is dissolved in the alcohol. The alcohol mixture in the second container is added to the first container, mixing until uniform. While mixing, the biotin is added. Sodium hydroxide is then slowly added to the mixture to achieve a pH of about 5. Finally, more purified water is added to bring the mixture to final weight.

What is claimed is:

1. A method for treating ungual pathologies in humans comprising topically applying to the affected unguis an effective amount of biotin or a pharmaceutically acceptable salt thereof.

2. The method according to claim 1 wherein the biotin or pharmaceutically acceptable salt thereof is topically applied to the affected unguis from one to six times daily.

3. The method according to claim 1 wherein the biotin or pharmaceutically acceptable salt thereof is applied in combination with an ungually acceptable pharmaceutical carrier.

4. The method according to claim 3 wherein the amount of biotin or pharmaceutically acceptable salt thereof is from about 0.01 to about 20.00% by weight of the total composition.

5. A method for hardening ungues in humans comprising topically applying to the ungues an effective amount of biotin or a pharmaceutically acceptable salt thereof.

* * * * *